United States Patent [19]
Nanci et al.

[11] Patent Number: 5,876,454
[45] Date of Patent: Mar. 2, 1999

[54] MODIFIED IMPLANT WITH BIOACTIVE CONJUGATES ON ITS SURFACE FOR IMPROVED INTEGRATION

[75] Inventors: Antonio Nanci, Dollard-des Ormeaux; Marc D. McKee, Pointe-Claire, both of Canada

[73] Assignee: Universite de Montreal, Quebec, Canada

[21] Appl. No.: 672,244

[22] Filed: Jun. 28, 1996

Related U.S. Application Data

[63] Continuation of Ser. No. 323,023, Oct. 14, 1994, abandoned, which is a continuation-in-part of Ser. No. 226,345, Apr. 12, 1994, abandoned, which is a continuation-in-part of Ser. No. 58,753, May 10, 1993, abandoned.

[51] Int. Cl.$^6$ .......................... A61K 2/28; A61K 38/18; A61K 38/39; B05D 3/04
[52] U.S. Cl. ........................ 623/16; 514/12; 514/21; 106/124; 204/129.95; 530/350; 530/395; 530/402; 427/2; 427/327; 427/337; 427/338
[58] Field of Search .................... 530/395, 350, 530/402; 427/2, 327, 337, 338; 204/129.95; 106/124; 514/12, 21; 623/16

[56] References Cited

U.S. PATENT DOCUMENTS

| | | | |
|---|---|---|---|
| 3,605,123 | 9/1971 | Hahn | 3/1 |
| 3,855,638 | 12/1974 | Pilliar | 3/1 |
| 4,038,702 | 8/1977 | Sawyer | 3/1.5 |
| 4,272,855 | 6/1981 | Frey | 3/1.9 |
| 4,336,618 | 6/1982 | Raab | 3/1.913 |
| 4,365,359 | 12/1982 | Raab | 3/1.912 |
| 4,372,831 | 2/1983 | Rosswag | 204/129.8 |
| 4,652,459 | 3/1987 | Engelhardt | 427/2 |
| 4,788,176 | 11/1988 | Wierserman et al. | 502/104 |
| 4,795,475 | 1/1989 | Walker | 623/66 |
| 4,973,493 | 11/1990 | Guire | 427/2 |
| 4,979,959 | 12/1990 | Guire | 623/66 |
| 5,045,318 | 9/1991 | Tengvall | 424/422 |
| 5,152,993 | 10/1992 | Bjursten et al. | 424/422 |
| 5,205,921 | 4/1993 | Shirkanzadeh | 205/318 |
| 5,211,663 | 5/1993 | Kovacs et al. | 623/16 |
| 5,217,492 | 6/1993 | Guire | 623/11 |
| 5,258,041 | 11/1993 | Guire et al. | 623/66 |
| 5,263,992 | 11/1993 | Guire | 623/66 |
| 5,328,955 | 7/1994 | Rhee et al. | 525/54.1 |
| 5,344,425 | 9/1994 | Sawyer | 606/198 |
| 5,350,800 | 9/1994 | Verhoeven et al. | 525/54.2 |
| 5,356,433 | 10/1994 | Rowland et al. | 623/11 |

FOREIGN PATENT DOCUMENTS

| | | |
|---|---|---|
| A-0 109 061 | 5/1984 | European Pat. Off. . |
| WO-A-9000887 | 2/1990 | WIPO . |

OTHER PUBLICATIONS

P. Connolly, *Tibtech,* 12:123–127, Apr. 1994.

McKinney et al. *J. Dent. Educ.,* (Sp. Iss.) 52:699–705, 1988.

Boskey, *Bone Mineral,* 6:111–123, 1989.

Sawada et al., *J. Perio. Res.,* 25:372–376, 1990.

Salonen et al., *J. Perio. Res.,* 26:355–360, 1991.

Timpl, *Eur. J. Biochem.,* 180:487–502, 1989.

Sukenik, C.N. et al., *J. Biomed. Materials Res.,* 24:1307–1323, 1990.

M. Volmer–Uebing et al., *Applied Suface Science,* 55:19–35, 1992.

Gorski, *Calcif. Tissue Int.,* 50:391–396, 1992.

McKee et al., *Anat. Rec.,* 234:479–492, 1992.

McKee et al., *J. Bone Miner. Res.,* 8:485–496, 1992.

Butler, *Connect. Tissue Res.,* 23:123–136, 1989.

Butler, *J. Biol. Buccale,* 19:83–89, 1991.

Schroeder, *Helv. Odont. Acta,* 13:65–83, 1969.

Schroeder, *Differentiation of human oral stratified epithelia,* S. Karger Publishers, Basel., 1981.

Zalzal et al., *J. Dent. Res.,* 72:411, 1993.

Lowry et al., *J. Biol. Chem.,* 164:321, 1946.

Hormia et al., *J. Dent. Res.,* 71:1503–1508, 1992.

Steflik et al., *J. Biomed. Materials Res.,* 26:529–545, 1992.

Telios Pharmaceuticals, Inc., *Manual for Summary*:1–10.

*Primary Examiner*—Chhaya D. Sayala
*Attorney, Agent, or Firm*—Evenson, McKeown, Edwards & Lenahan, PLLC

[57] ABSTRACT

The present invention relates to a bioactive conjugate adapted to coat a metal implant outer surface, which has the following structural formula I:

$$—R—X—P \qquad \qquad I$$

wherein,

R is O or S, adapted to be covalently attached to an implant surface;

X is selected from a bond, linear or branched chains of 1 to 30 covalently attached atoms of at least C, N, O Si or S, rings of 1 to 20 covalently attached atoms of at least C, N, O Si or S, and a combination thereof; and P is a bioactive molecule moiety which promotes tissue growth, stabilization and integration, and wherein said moiety retains its biological activity.

20 Claims, 9 Drawing Sheets

MODIFIED IMPLANT WITH BIOACTIVE CONJUGATES ON ITS SURFACE FOR IMPROVED INTEGRATION

RELATED APPLICATION

This application is a continuation of application Ser. No. 08/323,023 filed on Oct. 14, 1994, now abandoned, which is a continuation-in-part of application Ser. No. 08/226,345 filed on Apr. 12, 1994, abandoned, which is a continuation-in-part of application Ser. No. 08/058,753 filed on May 10, 1993 abandoned.

BACKGROUND OF THE INVENTION (a) Field of the Invention

The invention relates to bioactive conjugates covalently attached on an implant surface for improving its integration into surrounding tissues.

(b) Description of Prior Art

Devices in the form of plates, nails, pins, screws, and specially formed parts are commonly implanted into the skeletal structure of humans as artificial prosthetic means for permanent replacement of missing structural parts, or as permanent anchoring devices for maintaining a fixed relationship between the portions of a fractured bone. Clearly, in those situations where durability is necessary or desirable, the implanted part should remain permanently adhered to the contacting bone surface. This requirement has been a source of some difficulty in the past, where prosthetic parts composed of high strength materials such as titanium, stainless steel, tantalum, or Vitallium™ (an alloy of cobalt, chromium, and molybdenum) have generally been found incapable of forming a strong union with the natural bone structure into which the implantation is made. Highly magnified photographs of sections taken through bone and implant where failure has occurred have revealed what appears to be an absence of coalescence between the artificial and natural parts, and in fact an actual separation between the implant surface and the bone matter adjacent thereto is often apparent.

The use of surgical prosthetic devices, otherwise known as implants, is well known in various surgical applications, such as reconstructive surgery, for example, in the replacement of hip joints or the like. These applications generally involve the use of an implant constructed of metal or alloy which is not substantially corroded or otherwise degraded by body fluids. These prior implants, however, suffer from a number of limitations.

Typically, in the setting of broken bones, metal plates have been used which are secured to either side of the bone fracture. The plates are commonly secured to the bones by screws. While the plate in time becomes encapsulated in bone and body tissue, no bond is formed between the implant and the tissue. If one of the screws comes loose, the patient may have to undergo additional corrective surgery.

Suggestions have been made in the prior art to provide surgical prosthetic devices which are capable of permanent incorporation into the body, usually the bone, with bonding between the implant and the tissues.

In one prior suggestion, there is described a prosthetic device consisting of a metal substrate or base having a thin porous coating of metal overlying and bonded to the surface. The presence of the pores allows the soft or hard tissue to grow into the porous coating of the device and hence achieve mechanical incorporation into the body.

The only method of forming the coating which is described in this prior art suggestion is the technique of plasma or flame spraying onto the metal substrate. The result of this process is a densely adherent layer of the sprayed metal on the substrate metal with no porosity or practically no porosity at the interface between the coating and the substrate and with gradually increasing porosity, including increasing pore size and decreasing density, from the interface to the surface of the coating.

While this technique may be effective in providing a porous coating on a metal substrate, nevertheless the technique results in a very serious drawback in the finished prosthetic device. In tests designed to show the ingrowth of tissue into the coated surface of the device, a pin, having the coating thereon, and after embedding in a bone for a period of time, was subjected to a pull-out test. This pull-out test resulted in shearing at the interface between the coating and the base metal. This result indicates that the overall strength of the device is less than that of the bone. Quite clearly, the provision of a device weaker than the bone to which it is attached could result in failure of the device due to shearing at the interface with harmful and painful consequences for a patient who is treated using such a device.

Another prior art suggestion involves the provision of a prosthetic device constructed of porous ceramic material. This material is structurally weak and attempts to overcome this defect by filling the bulk of the device with resin material, leaving a porous surface area. Although the presence of the resin may increase the strength of the central portion of the device, the surface region remains weak. Further, the presence of resin material degradable by body fluids would lead to unsatisfactory use in the human body. In addition, the maximum pore size for the ceramic is indicated to be 50 microns, and much smaller sizes are preferred. If the pore size were greater than 50 microns, then the structure would become too weak for effective use.

It has been known to anchor surgical implants in bones with the use of cements. It has also been known to improve the anchorage of an implant without using a cement by constructing the implant so as to receive an ingrowth of bone tissue. For example, implants have been provided with a porous surface of a certain depth. However, these porous surface implants have not proven themselves in practice since the mechanical strength of the anchoring surface is greatly affected in an adverse sense. The reason for this weakening of the material is that the pores produce sharp corners and edges in the material. This leads, especially in the case of long-term alternating stresses, to cracks which continue into the solid core of the implant and eventually to fatigue fractures.

Implants have also been constructed with a regular arrangement of bosses and/or depressions in order to improve mechanical adhesion within bones. However, quite apart from the fact that sharp corners and edges have not been avoided in these structures, increased adhesion between the implants and the tissue has not been achieved. This latter failure has occurred because only an insufficient increase of the surface is obtained. As is known, an increase in the anchoring surface is a decisive feature which can influence and improve a bond between the tissue and the anchoring part of the implant which acts as a foreign body therein.

U.S. Pat. No. 3,605,123 in the name of Hahn (Apr. 29, 1969) describes a prosthesis of high structural strength, with a capability of promoting substantially complete integration with the bone structure in which it is implanted.

U.S. Pat. No. 3,855,638 in the name of Pilliar (Dec. 24, 1974) describes a surgical prosthesis of a composite structure consisting of a solid metallic material substrate and a porous coating adhered to and extending at least partially over the surface of the substrate. The porous coating on the surface of the substrate has several parameters which are essential to the provision of a satisfactory device free from the defects of the prior devices.

U.S. Pat. No. 4,272,855 in the name of Frey (Jun. 16, 1981) describes a bone implant with an anchoring surface including a plurality of villi.

However, none of these prior art implants is provided with a chemical coating which would promote a chain of biochemical reactions at the tissue-implant interface, thereby promoting tissue growth, stabilization and integration of the implant.

Substantial progress has been made with regard to implants such as for the restoration of oral tissues, and currently employed techniques rely principally on the use of alloplastic replacement materials. Titanium, titanium-alloy and hydroxyapatite-coated orthopedic and dental implants are widely used in medicine and dentistry for tissue repair, reconstruction and replacement, and as supports for various prostheses. These implants are generally utilized in surgical procedures involving bone, where they are incorporated into this hard, mineralized tissue ('osseointegration'), and in some cases, also traverse soft tissue such as skin or the mucosa of the oral cavity.

In hard biological structures such as teeth (dentin, cementum) and bone, great rigidity and strength are imparted to these tissues by an extensive network of collagen protein fibers that are impregnated with apatitic mineral. Although collagen is by far the most abundant protein in these tissues, other non-collagenous proteins are also secreted by cells and accumulate within their respective extracellular matrices. Although, the exact function of these non-collagenous proteins is unknown, they have recently come under intense scrutiny since experimental results indicate that they may play a critical role in the initiation and regulation of calcification (reviewed by Boskey, *Bone Mineral*, 6:111–123, 1989 and Gorski, *Calcif. Tissue Int.*, 50:391–396, 1992).

One group of non-collagenous proteins, the phosphoproteins (containing organic phosphorus), and more specifically a dentin phosphoprotein called phosphophoryn and two bone phosphoproteins named osteopontin and bone sialoprotein (reviewed by Butler, *Connect. Tissue Res.*, 23:123–136, 1989 and Butler, *J. Biol. Buccale*, 19:83–89, 1991), may participate by acting as a seed or regulator of mineral crystal growth and/or by directing cells and their associated functions to specific sites within the tissue. In addition to its co-localization with mineral at early sites of calcification, osteopontin and bone sialoprotein are known to contain the Arg-Gly-Asp (RGD) cell-binding peptide sequence that binds to a plasma membrane integrin receptor and promotes cell attachment (see *Telios Pharmaceuticals, Inc., Manual for Summary:* 1–10). The presence of this triplet sequence, the distribution of these proteins, and their association with mineral, suggest that these phosphoproteins may have a multifunctional role during mineralized tissue formation whereby they may, firstly, initiate and regulate mineralization, and secondly, direct dynamics by mediating cell attachment to the matrix (McKee et al., *Anat. Rec.*, 234:479–492, 1992 and McKee et al., *J. Bone Miner. Res.*, 8:485–496, 1992).

For an implant to be successful, the intraosseous portion of the implant must undergo osseointegration and a functional junctional epithelium-like seal must form around the transgingival portion (reviewed by McKinney et al., *J. Dent. Educ.*, (Sp. Iss.) 52:696–705, 1988). Any imperfection in these events may lead to the eventual rejection of the implant. The junctional epithelium, in normal conditions, seals the subgingival portion of the tooth from the buccal environment and consists of an epithelial layer, a glycoproteinaceous structure which resembles a basal lamina, and hemidesmosomes (Schroeder, *Differentiation of human oral stratified epithelia*, S. Karger Publishers, Basel., 1981). The basal lamina and the hemidesmosomes are believed to serve in the attachment of the gingiva to the tooth surface (Schroeder, *Helv. Odont. Acta*, 13:65–83, 1969), possibly via integrin receptors (Hormia et al., *J. Dent. Res.*, 71:1503–1508, 1992). It has been suggested that laminin (Sawada et al., *J. Perio. Res.*, 25:372–376, 1990) and collagen type VIII (Salonen et al.,*J. Perio. Res.*, 26:355–360 1991) are present in the junctional epithelium, the presence of the latter being particularly interesting in that collagen type VIII is not a common component of basement membranes in general. Similarly, the sugar content of the junctional epithelium basal lamina, as visualized by lectin-gold cytochemistry (Zalzal et al., *J. Dent. Res.*, 72:411, 1993), appears to be unique. Just like conventional basement membranes, the basal lamina of the junctional epithelium could play an inductive role in the specialization of the oral epithelium to become bona fide junctional epithelium (reviewed by Timpl, *Eur. J. Biochem.*, 180:487–502, 1989).

The fundamental assumption in each of these situations is that extracellular matrix components of the adjacent tissue (i.e. bone, soft connective tissues or epithelium) allow 'bonding' between the non-biological implant and the biological extracellular matrix surrounding the implant. In bone, for example, this bonding region (interface) has been identified, using electron microscopy, as a layer of non-collagenous organic material separating the bone matrix proper from the implant (Steflik et al., *J. Biomed. Materials Res.*, 26:529–545, 1992).

Sukenik, C. N. et al. (*J. Biomed. Materials Res.*, 24:1307–1323, 1990) describes the modulation of cell adhesion by modification of titanium surfaces with covalently attached self-assembled monolayers. However, they do not show the attachment of bioactive conjugates which include biologically active molecules to promote tissue growth, stabilization and integration at the tissue-implant interface.

It would be highly desirable to have a chemical coating for metal implants which would mimic the biological activity of the natural proteins found at the tissue-implant interface in the healing patient with an integrated implant, based on normally-occurring biochemical and physiological mechanisms.

It would be highly desirable to have a chemical coating for metal implants which would promote a chain of biochemical reactions at the tissue-implant interface, thereby promoting tissue growth, stabilization and integration of the implant.

SUMMARY OF THE INVENTION

One aim of the present invention is to provide a chemical coating for metal implants which would mimic the biological activity of the proteins found at the tissue-implant interface in the healing patient with an integrated implant, based on normally-occurring physiological mechanisms.

Another aim of the present invention is to provide a bioactive conjugate which would promote a chain of biochemical reactions at the tissue-implant interface, thereby promoting tissue growth, stabilization and integration of the implant.

In accordance with the present invention there is provided a bioactive conjugate adapted to coat a metal implant outer surface which have the following structural formula I:

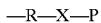

wherein,

R is O or S, adapted to be covalently attached to an implant surface;

X is selected from a bond, linear or branched chains of 1 to 30 covalently attached atoms selected from the group consisting of C, N, O, Si or S or other linking atoms, rings of 1 to 20 covalently attached atoms selected from the group consisting of C, N, O, Si or S or other linking atoms and a combination of rings and chains of similar composition; and P is a covalently-attached bioactive molecule moiety which promotes tissue growth, stabilization and integration, and wherein the moiety retains its biological activity.

More particularly, in accordance with the present invention, X is selected from one of the following possibilities: a direct bond to a bioactive molecule; a linear alkyl $C_1$–$C_{30}$ chain, terminated by COOH, $NH_2$, OH, SH or other functional groups chosen to permit covalent linking to a bioactive molecule; a linear chain consisting of 1–20 atoms of C interspersed with 1–10 atoms of N, O or S, terminated by COOH, $NH_2$, OH, SH or other functional groups chosen to permit covalent linking to a bioactive molecule; a linear alkylsilyl $SiC_1$–$SiC_{30}$ chain, terminated by COOH, $NH_2$, OH, SH or other functional groups chosen to permit covalent linking to a bioactive molecule; or rings composed of C and/or N, connected directly to a bioactive molecule or connected by means of linear chains of C, N, O or S atoms, terminated by COOH, $NH_2$, OH, SH or other functional groups chosen to permit covalent linking to a bioactive molecule.

The X moiety of the bioactive conjugate is selected depending on the desired P moiety which is to be attached to an implant and is chosen according to the desired spacing distance of the P moiety from the implant.

The preferred X moieties in accordance with the present invention are $C_2$–$C_{12}$ alkyl, which may be substituted or non-substituted, $SiC_3$–$SiC_{12}$, which may be substituted or non-substituted, and 1,3,5-triazine (cyclic $C_3N_3$), which may be substituted or non-substituted.

The X moiety may be substituted with a substituent selected from the group consisting of COOH, $NH_2$, OH, SH, Cl or other groups chosen to permit covalent linking to a bioactive molecule.

In accordance with the present invention there is provided a bioactive conjugate adapted to coat a metal implant outer surface.

Further, the bioactive conjugate of the present invention may be forming a self-assembling monolayer on the implant surface.

The coating of the metal implant in accordance with the present invention, in addition to covalently attaching the bioactive molecule moiety which promotes tissue growth, stabilization and integration onto the implant surface, inhibits the contamination of the metal implant surface.

More particularly, in accordance with the present invention, P is selected from normal and/or derivatized osteopontin, bone sialoprotein, bone acidic glycoprotein-75, osteocalcin, osteonectin, bone morphogenetic proteins, transforming growth factors, laminin, type IV collagen, type VIII collagen, enamel proteins (amelogenins and non-amelogenins), $α_2$HS-glycoprotein, fibronectin, cell adhesion peptides, prostaglandin, serum proteins, glucocorticosteroids (dexamethasone), phosphate, phosphoserine, pyrophosphates, phosphothreonine, phosvitin, phosphophoryn, biphosphonates, phosphonates, phosphatases, sulfonates, sulfates, carboxy group, bone and epithelial proteoglycans, mineral and cell binding peptide sequences such as Arginine-Glycine-Aspartic acid (Arg-Gly-Asp), polyaspartate, and other biological molecules capable of promoting tissue integration, and non-biological molecules chosen to imitate these effects.

In accordance with the present invention the expression "metal implant" is intended to mean any surgical implant material made of solid metal or of a metal sheet or foil, or an implant material having at least one side or one surface coated with metal.

More particularly, in accordance with the present invention, the metal implant is made of titanium, stainless steel, tantalum, Vitallium™ or any other medically acceptable metallic implant material.

The modified metal surfaces, as in the present invention, may be used for the micro- or nanofabrication of molecular patterns or arrays of molecules, which are herein referred to as "molecular integrated circuit". This form of molecular integrated circuits may have applications in fields such as biosensors, bioelectronics and molecular electronics.

DETAILED DESCRIPTION OF THE INVENTION

The bioactive conjugates of the present invention, once coated on an implant, provide an attachment of biologically active molecules through a carbon chain bridge which promote tissue growth, stabilization and integration at the tissue-implant interface, and also provide protection against oxidation of the implant.

Furthermore, the bioactive conjugates of the present invention also provide for a flexible and resilient coating on the implant which serves to absorb the forces applied on the implant and which may help prevent lesions and fractures of the tissue at the tissue-implant interface.

The bioactive conjugates also provide for a better attachment of the implant at soft tissue (epithelial cells) or hard tissue (bone) sites.

Figure 1:
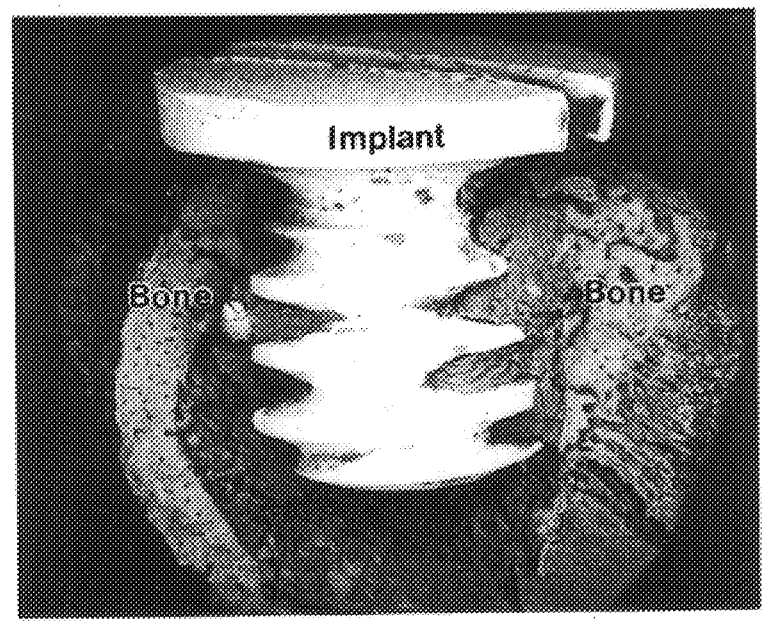
FIG. 1 is a scanning electron micrograph of a titanium screw implant in situ in a rat tibia bone model.

FIG. 1 illustrates the tissue-implant interface of a non-coated implant in situ in bone.

Figure 2:
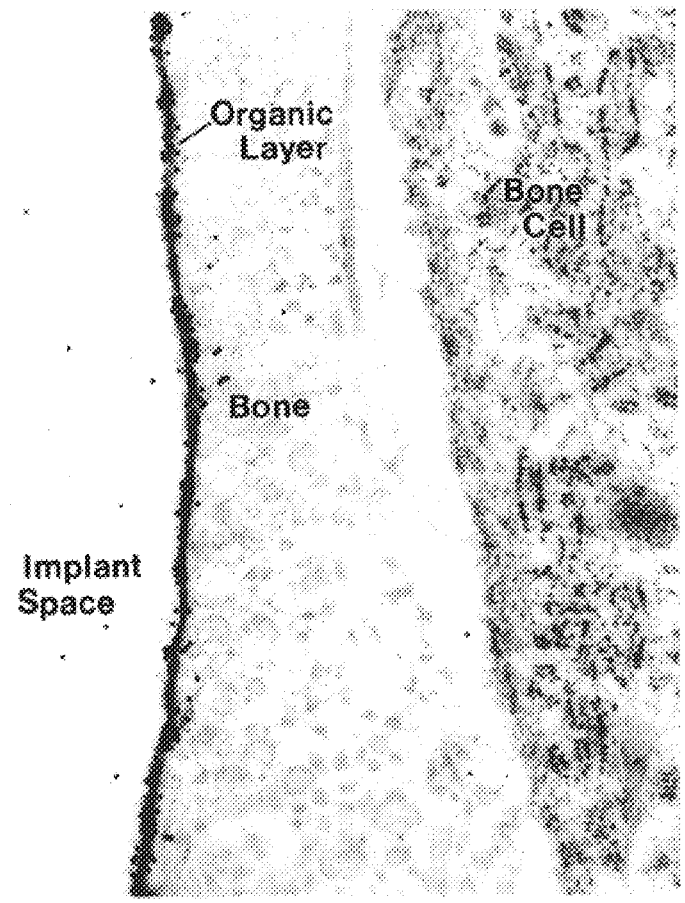
FIG. 2 is a transmission electron micrograph of the tissue-implant interface in a tibial bone showing an accumulation of organic material immunolabeled for the bone protein osteopontin.

A thin layer at the bone-implant interface can be observed at higher magnification by electron microscopy in FIG. 2, which was identified as containing a naturally occurring bone protein known as "osteopontin". Thereafter, in accordance with the present invention, a preferred protein for coating an implant is osteopontin.

Figures 9A, 9B:
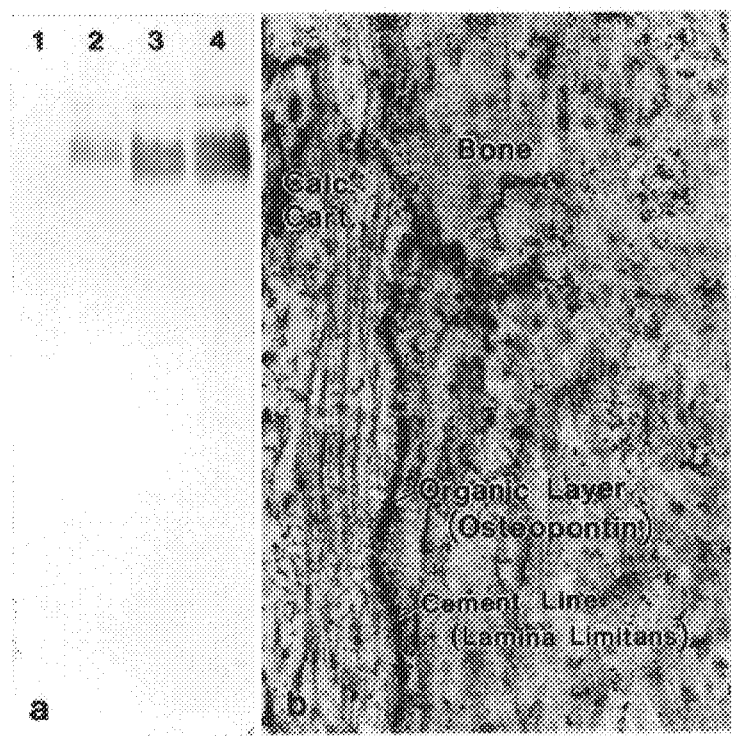
FIG. 9A illustrates an immunoblot with a polyclonal anti-osteopontin antibody raised in chickens and purified from egg yolks.
FIG. 9B illustrates immunocytochemical labeling for rat osteopontin at the interface between calcified cartilage and bone in the rat tibial growth plate using the same anti-osteopontin antibody as used for FIG. 9A.

FIG. 9A illustrates an immunoblot with an antibody against osteopontin raised in chickens and purified from egg yolk. The polyclonal anti-osteopontin antibody was raised against osteopontin purified from rat bone. Lane 1, rat serum albumin; Lane 2, total HCl/guanidine bone extract; Lane 3, purified rat bone osteopontin; Lane 4, purified rat bone osteopontin donated by Drs. M. C. Farach-Carson and W. T. Butler (University of Texas, Houston).

FIG. 9B illustrates immunocyochemical labeling for rat osteopontin in the rat tibia using the anti-osteopontin antibody and demonstrating the concentration of this protein, as visualized by the accumulation of gold particles over an organic layer, referred to as the "cement line" or "lamina limitans", at a natural, matrix-matrix (calcified cartilage-bone) interface as found in normal tissues (McKee et al., Anat. Rec., 234:479–492, 1992; McKee et al., J. Bone Miner. Res., 8:485–496, 1992).

This interface represents the junction between two spatio-temporally distinct matrices created during normal long bone growth where bone is deposited by osteoblasts onto a "scaffolding" of calcified cartilage. During bone remodeling, this same layer of protein is also found at bone-bone interfaces ("cement lines"). It is thus proposed that osteoblasts behave similarly when encountering a titanium "substrate" and secrete an osteopontin-containing, organic layer at the bone-titanium interface (FIG. 10);

FIG. 10 illustrates when a tooth erupts into the oral cavity, part of the reduced enamel organ is believed to fuse with the gingiva to form the functional epithelium (Schroeder and Listgarten, Monographs in Developmental Biology, Ed. A. Wolsky, Tarrytown, N.Y., Vol.2:1–127, 1971). More specifically, the "basal lamina" separating the maturation stage ameloblasts from the enamel surface shows characteristics similar to the internal basal lamina of the junctional epithelium, and may indeed, take part in the formation of the initial epithelial attachment (Nanci et al., Histochemistry, 99:321–331, 1993).

Maturation stage ameloblasts are post-secretory cells which produce little or no enamel proteins, and indeed, the basal lamina separating them from enamel does not seem to contain much of these proteins. However, it is well known that under certain conditions (epithelial pearls; intermediate cementum), epithelial cells related to tooth formation can be reactivated to produce enamel proteins.

Consistent with the epithelial origin of the attachment, cells of the junctional epithelium were examined to determine whether they are able to express enamel proteins. Enamel proteins consist essentially of two classes of proteins, amelogenins and non-amelogenins (enamelins) both of which undergo substantial extracellular processing (reviewed in Nanci and Smith, Calcification in Biological Systems, Chapter 13: 313–343, 1992).

Figures 10A, 10B:
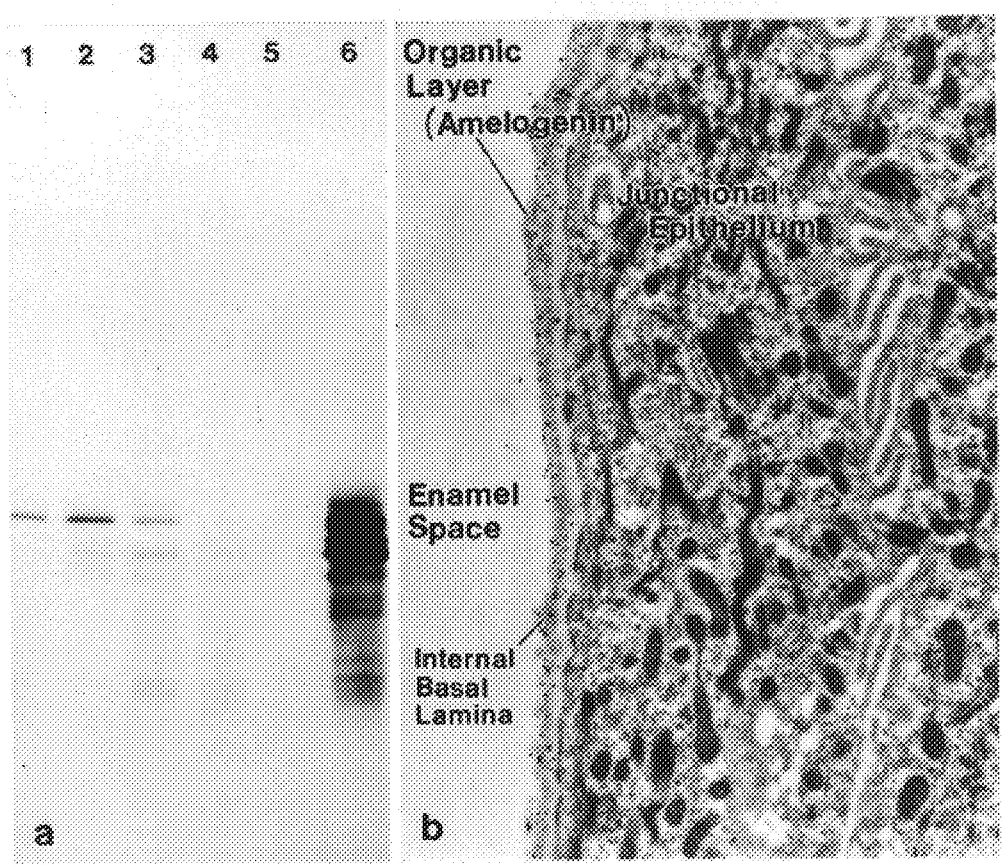
FIG. 10A is an immunoblot of intact proteins and degradation products in enamel organ and enamel matrix using rabbit anti-mouse amelogenin antibody.
FIG. 10B illustrates the immunodetection of enamel proteins in the organic layer between the tooth surface and the junctional epithelium of rat molars.

An antibody raised in rabbits against recombinant mouse amelogenin protein expressed in E. coli (courtesy of the laboratory of Dr. H. C. Slavkin, Center for Craniofacial Molecular Biology, University of Southern California) was used to immunolocalize enamel proteins. Recently, proteins from rat incisor enamel were purified and antibodies to these proteins were raised in the chicken (purified from the egg yolk; in collaboration with Dr. C. E. Smith, McGill University). The rabbit anti-mouse amelogenin recognizes intact proteins and degradation products found between 14 and 31 kDa in ameloblasts (FIG. 10A, lanes 1–5) and enamel matrix (FIG. 10A, lane 6). Maturation stage ameloblasts (FIG. 10A, lanes 3–5) gradually stop producing enamel proteins.

Enamel proteins are immunodetected in the organic layer (internal basal lamina) between the tooth surface and the junctional epithelium of rat molars (FIG. 10B). Since so far it has not been possible to clearly demonstrate the presence of typical basement membrane constituents in the internal basal lamina of the junctional epithelium, or as a matter of fact of in that related to maturation stage ameloblasts, the possibility exists that these basal laminae represent extracellular matrices related to basement membranes but with a distinct composition reflecting their specialized function, such as mediating cell differentiation and/or promoting soft tissue-hard tissue adhesion.

In accordance with the present invention, it is proposed to use components of the internal basal lamina, and in particular enamel proteins, as a surface coating on the transgingival portion of titanium implants to promote cell differentiation and the formation of a functional and stable epithelial seal around the implant.

The process, in accordance with the present invention for coating a metal implant with a bioactive conjugate, comprises the following steps.

First, a metal implant surface is cleaned and deoxidized by effecting a potentiostatic electrochemical polishing in a perchloric acid-butanol-methanol solution similar to that described by M. Volmer-Uebing et al. (*Applied Surface Science*, 55:19–35, 1992). The preparation of low-oxide metal surfaces at room temperature is by polarizing the metal in 1M perchloric acid ($HClO_4$) at a potential of 40V. Under these conditions the metal is in a thermodynamically stable phase. The deoxidized surface may then be reoxidized also by potentiostatic electrochemical polarization in a phosphate buffer at 6 V.

Second, the cleaned deoxidized or controlled re-oxidized implant surface is contacted with compounds that cause covalent coating with a bioactive conjugate of the present invention.

Theoretical Coverage of Surface with Sulfur
  a) perfect crystal (flat surface)

The surface concentration of titanium (Ti) is about $1.6 \times 10^{15}$ atoms/cm$^2$ and the diameter of sulfur (S) is about 2×diameter of Ti, thus the surface concentration of sulfur atoms is about $0.8 \times 10^{15}$ atoms/cm$^2$ and each sulfur atom is attached to a chain of 18 carbon atoms of about 15 Å long.

Because the depth analyzed is 45 Å, the surface concentration of carbon atoms is about $1.4 \times 10^{16}$ atoms/cm$^2$, that is about 18 times the surface concentration of sulfur atoms).

Depth probed ($\approx$45 Å)–length of thiolase ($\approx$15 Å)=30 Å

30 Å Ti$\approx$11 monolayers$\approx 1.8 \times 10^{16}$ atoms/cm$_2$

Ti:S:C=$1.8 \times 10^{16}$:$0.8 \times 10^{15}$:$1.4 \times 10^{16}$=54.9%:2.4%:42.7% b) 45° sawtooth surface (rough surface, more realistic)

Ti:S:C=41.6%:2.8%:55.6% c) contaminated surface

Since titanium (Ti) is a reactive metal, it is difficult to clean and it gets recontaminated easily.

The realistic coverage of the Ti surface with S is <2.8%, this value depends on the extent of the contamination of the surface.

TABLE 1

Atomic percentages at reduced titanium surfaces following treatment with a functionalized alkanethiol

| Treatment | O | Ti | C | S |
|---|---|---|---|---|
| SH(CH$_2$)$_2$COOH | 35.7 | 7.3 | 53.9 | 2.1 |
| SH(CH$_2$)$_2$COOH/H$_2$O | 43.2 | 15.4 | 37.2 | 2 |

Table 1 above provides a comparison of chemically-treated reduced titanium surfaces before and after aqueous exposure.

Figure 11:
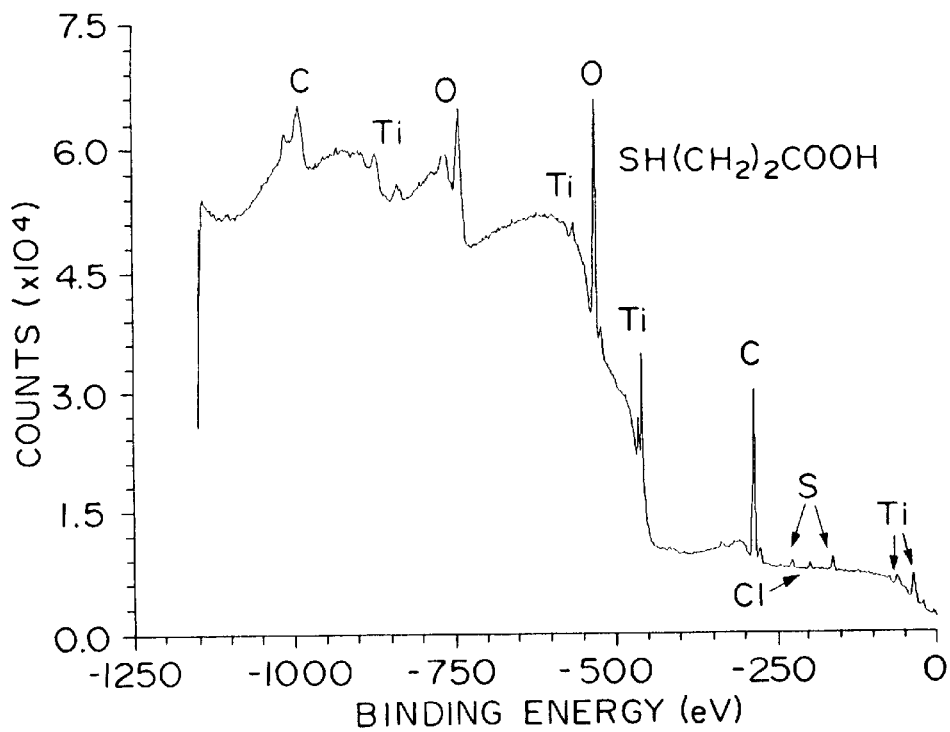
FIG. 11 is an XPS spectrum showing the presence of sulfur at the reduced titanium surface after treatment with a functionalized short-chain alkanethiol.

FIG. 11 demonstrates sulfur peaks indicating thiol binding to titanium.

Figure 12:
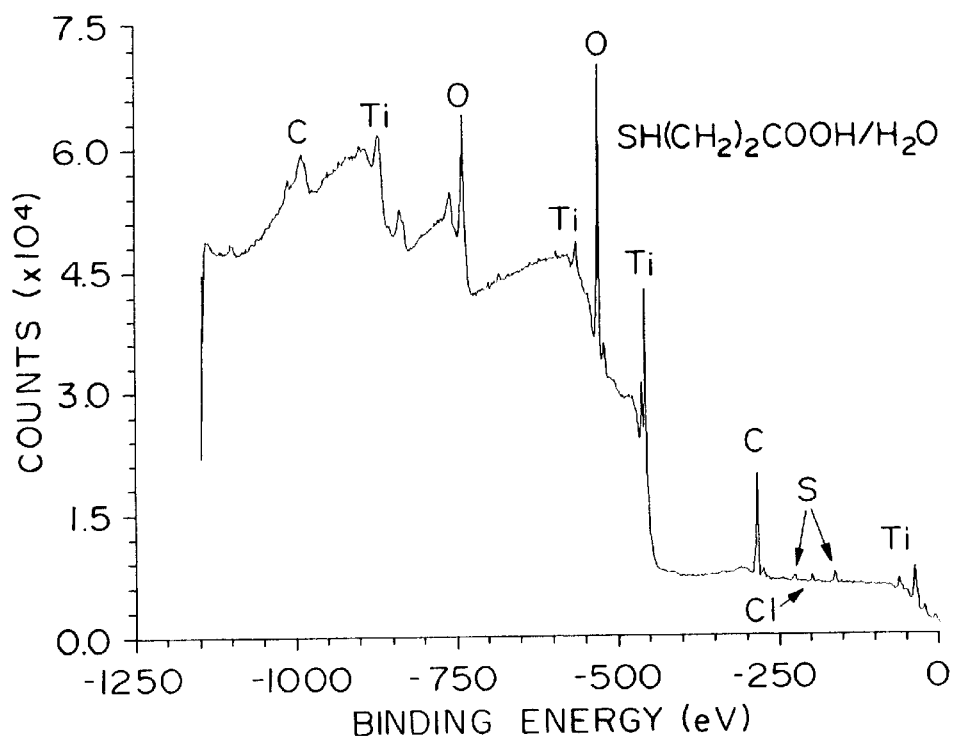
FIG. 12 is an XPS spectrum showing retention of sulfur and stability of the Ti—SH bonding following exposure of the alkane-treated titanium surface to water.

FIG. 12 shows no major change in the sulfur (thiol) peaks after aqueous treatment.

The present invention will be more readily understood by referring to the following examples which are given to illustrate the invention rather than to limit its scope.

EXAMPLE I

Coating of a Titanium Implant with Octadecyl Thiolate

Sample Preparation

The titanium metal substrate is cleaned by mechanical polishing with alumina 0.1 um followed by an ultrasonic chemical cleaning in pure acetone for about 15 min. The substrate is electrochemically polished in a perchloric acid-butanol-methanol solution in a 1:12:7 ratio by volume for 30 min. at about 40 V. This technique establishes the electrochemical conditions at which the surface contaminants are unstable, and are removed. While we have not attempted to optimize the experimental conditions, the technique, as used, causes a measurable cleaning of the titanium surface.

This is carried out in a $N_2$-flushed dry box which also contains $10^{-3}$ to $10^{-4}$M hexane solutions of octadecyl thiol, $CH_3-(CH_2)_{17}-SH$. Thus, without exposure to air, which is capable of re-contaminating the highly reactive clean titanium surface, the metal is submerged in the thiol solution overnight. This permits the thiol to react with the metal surface, forming self-assembling monolayers, such as $$\text{Ti surface} \begin{array}{l} -S-(CH_2)_{17}-CH_3 \\ -S-(CH_2)_{17}-CH_3 \end{array}$$

which extend above the metal surface by about 15 Angstroms. Samples were rinsed in hexane before analysis.

Analysis Technique

The surface analytical technique used is called X-ray Photoelectron Spectroscopy (XPS) or Electron Spectroscopy for Chemical Analysis (ESCA). It has the advantage that small differences in electron density at the emitting atom, caused by differences in chemical bonding, are reflected in small shifts in the energy of the emitted electron. Software has been developed which permits the computer manipulation of these data, allowing the separation of close-lying peaks for further study.

The depth probed at the titanium emission energy is about 45 Angstroms; for a perfectly flat titanium crystal covered with a monolayer of thiol, the depth probed into the titanium is, then, about 30 Angstroms. For a rougher surface, modeled on a 45° saw-tooth, this depth is closer to 20 Angstroms although the full thiolate monolayer is probed in both cases.

Results and Discussion

Figure 3:
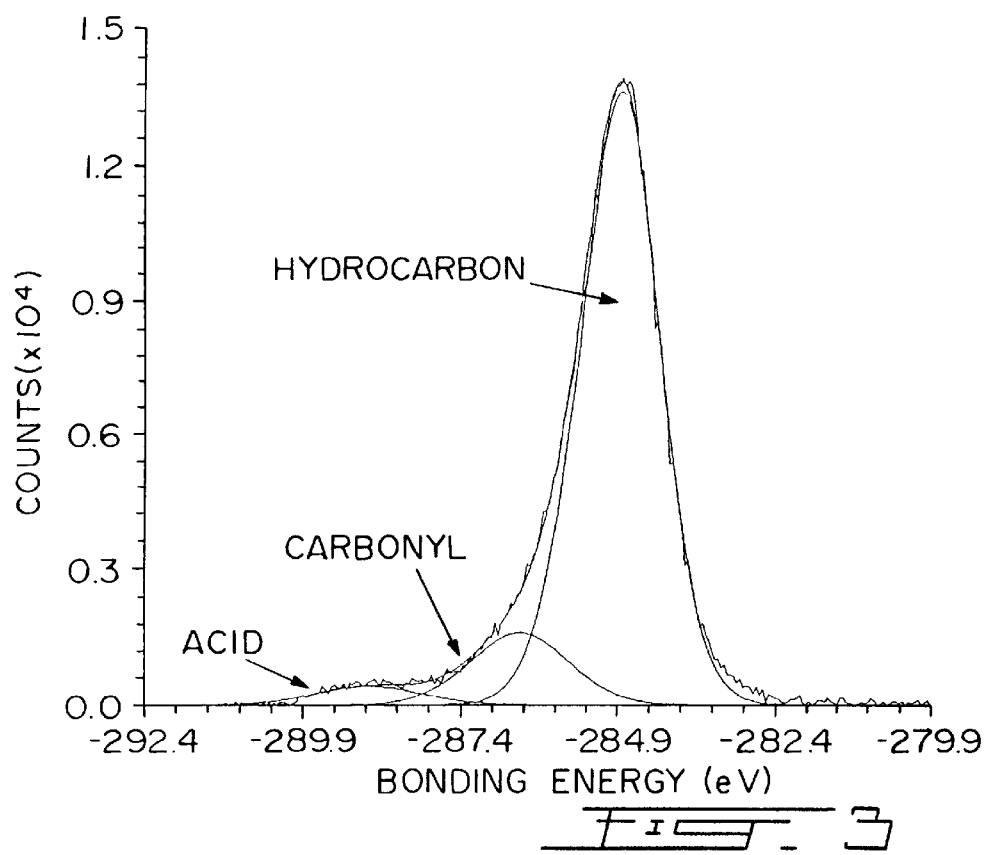
FIG. 3 represents the carbon spectrum obtained by X-ray Photoelectron Spectroscopy of the surface of a titanium implant which has reacted with a hexane solution of octadecyl thiol, showing the octadecyl thiolate attached thereto.
Figure 4:
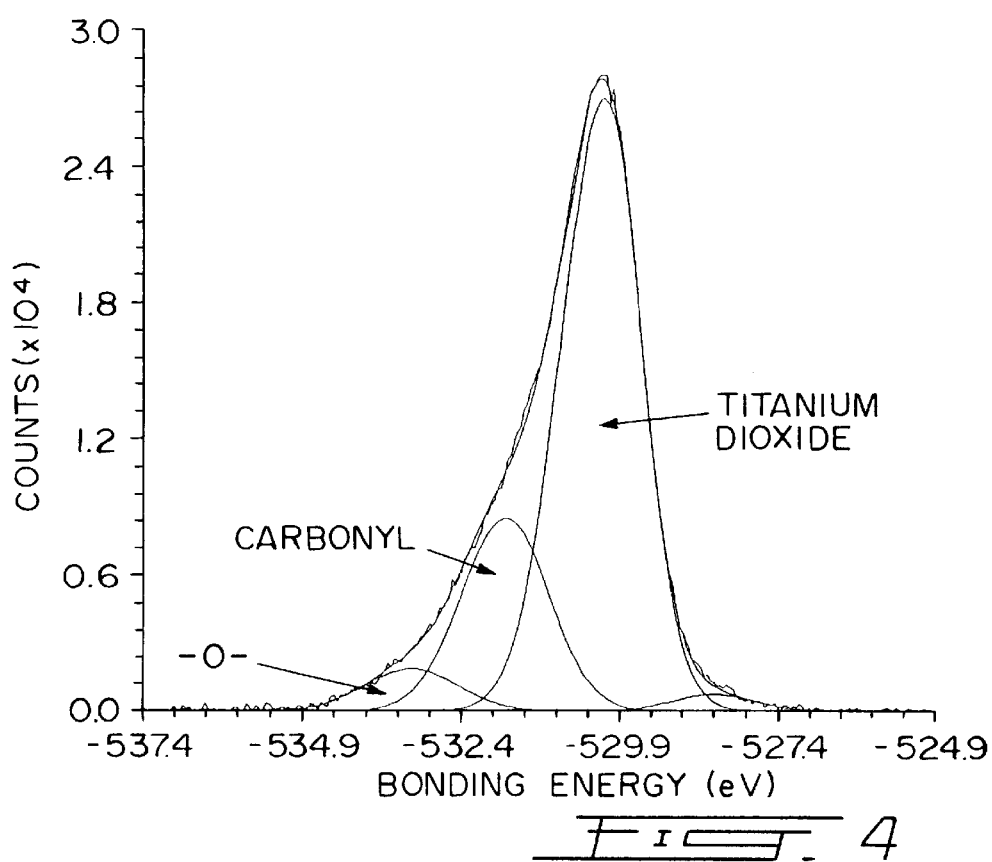
FIG. 4 represents the oxygen spectrum obtained by X-ray Photoelectron Spectroscopy of the surface of a titanium implant with octadecyl thiolate attached thereto.
Figure 5:
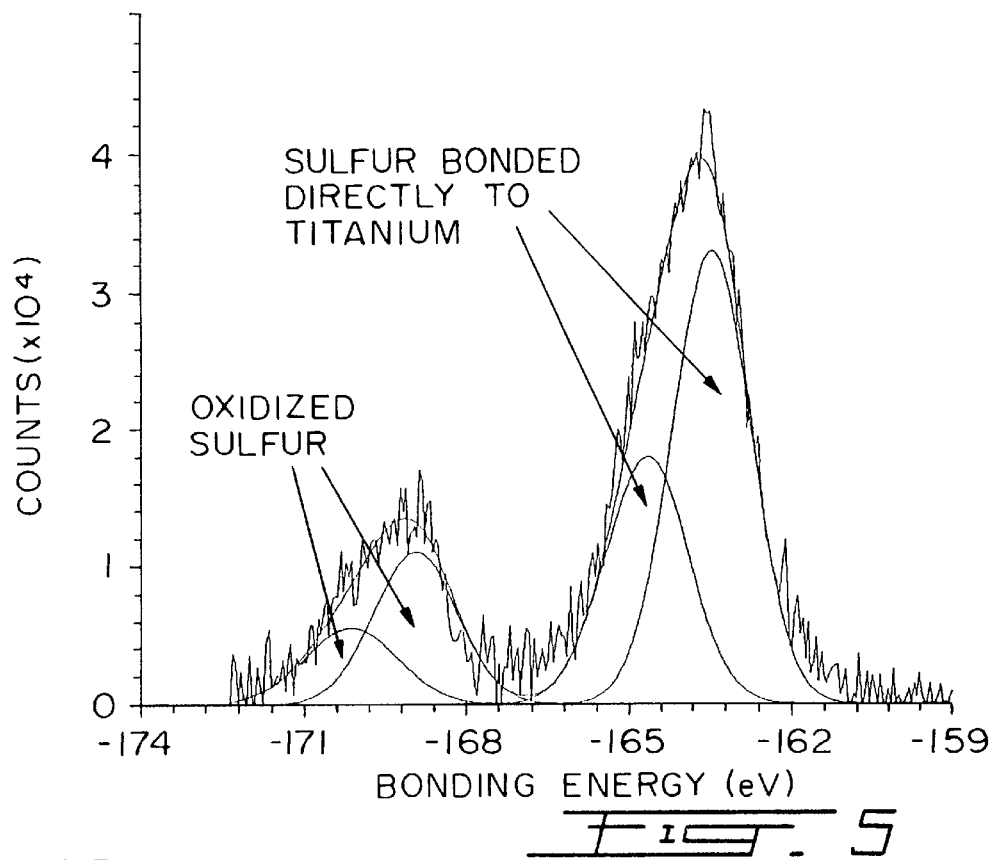
FIG. 5 represents the sulfur spectrum obtained by X-ray Photoelectron Spectroscopy of the surface of a titanium implant with octadecyl thiolate attached thereto.
Figure 6:
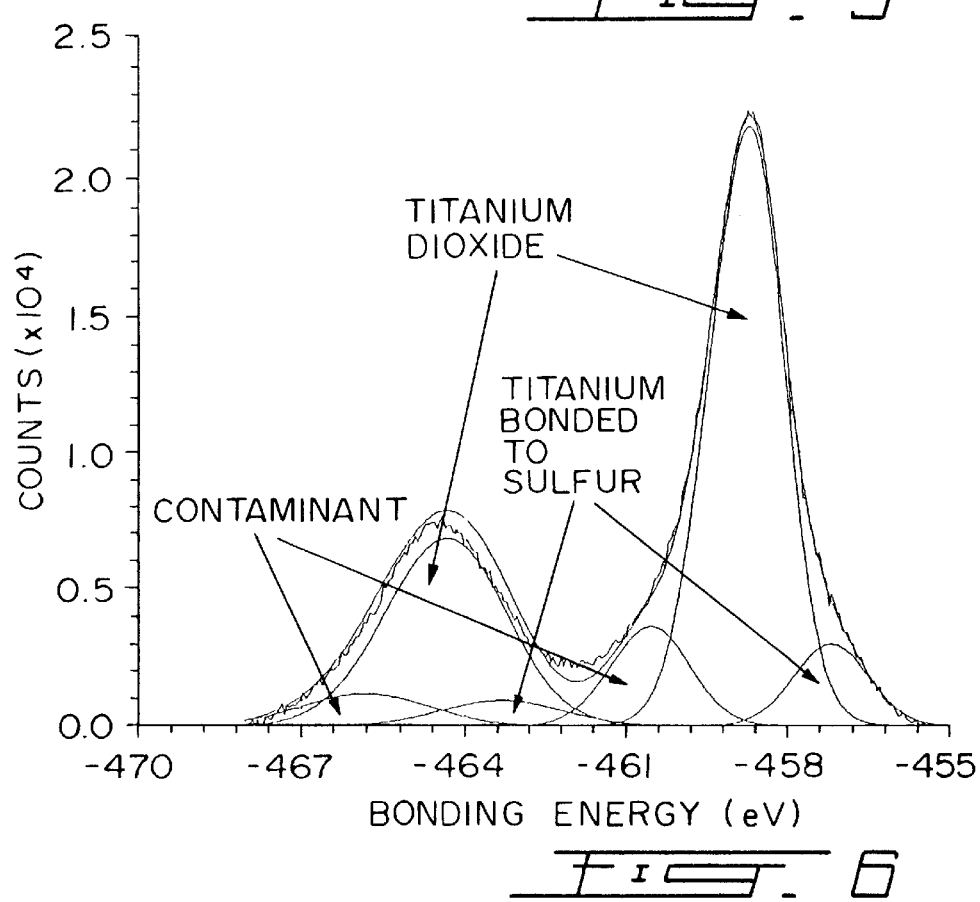
FIG. 6 represents the titanium spectrum obtained by X-ray Photoelectron Spectroscopy of the surface of a titanium implant with octadecyl thiolate attached thereto.

A typical set of spectra is seen in the accompanying FIGS. 3 to 6, where FIG. 3 is the carbon spectrum, FIG. 4 is the oxygen spectrum, FIG. 5 is the sulfur spectrum and FIG. 6 is the titanium spectrum. The peaks for carbon and oxygen arise from electrons emitted from s-type orbitals, meaning that each peak indicates another environment. Their probable attributions are indicated on the FIGS. 3 and 4.

On the other hand, the peaks for sulfur and titanium arise from electrons emitted from p-type orbitals, meaning that pairs of peaks indicate different environments. Again, probable attributions are indicated on the FIGS. 5 and 6.

The fact that titanium can clearly be detected indicates that only a monolayer of thiol was deposited. Variations in carbon and oxygen percentages, as well as in the various titanium components, indicates some point-to-point variability in cleaning and thiol deposition. However the thiol directly bonded to titanium appears impervious to attack by water vapor and by direct water immersion for at least 2.5 hours.

EXAMPLE II

Covalent Attachment with Thiol of Alkaline Phosphatase to a Titanium Implant

A cleaned titanium implant is coated with 16-aminohexadecanethiol by the general procedure described in Example I. The implant is then stirred for 60 min. at 25° C. under $N_2$ with a solution of glutaraldehyde in 0.1M phosphate buffer. The implant is then rinsed with buffer and stirred for 12 h at 25° C. with a solution of 3 mg alkaline phosphatase (from bovine intestinal mucosa, 5 units/mg) in 3 mL phosphate buffer. The implant is then rinsed with buffer. Enzymatic activity would be measured by the method of Lowry et al. (*J. Biol. Chem.*, 164:321, 1946).

EXAMPLE III

Covalent Attachment with Silane of Alkaline Phosphatase to a Titanium Implant A titanium implant was cleaned by the general procedure of Example I and subjected to controlled reoxidation. The implant was then stirred for 2 h under $N_2$ with a 10% solution of 3-aminopropyltriethoxysilane in refluxing toluene. The modified implant was then covalently coupled with alkaline phosphatase by the glutaraldehyde procedure described in Example II. Enzymatic activity was measured by the method of Lowry et al. (*J. Biol. Chem.*, 164:321, 1946).

Figure 7:
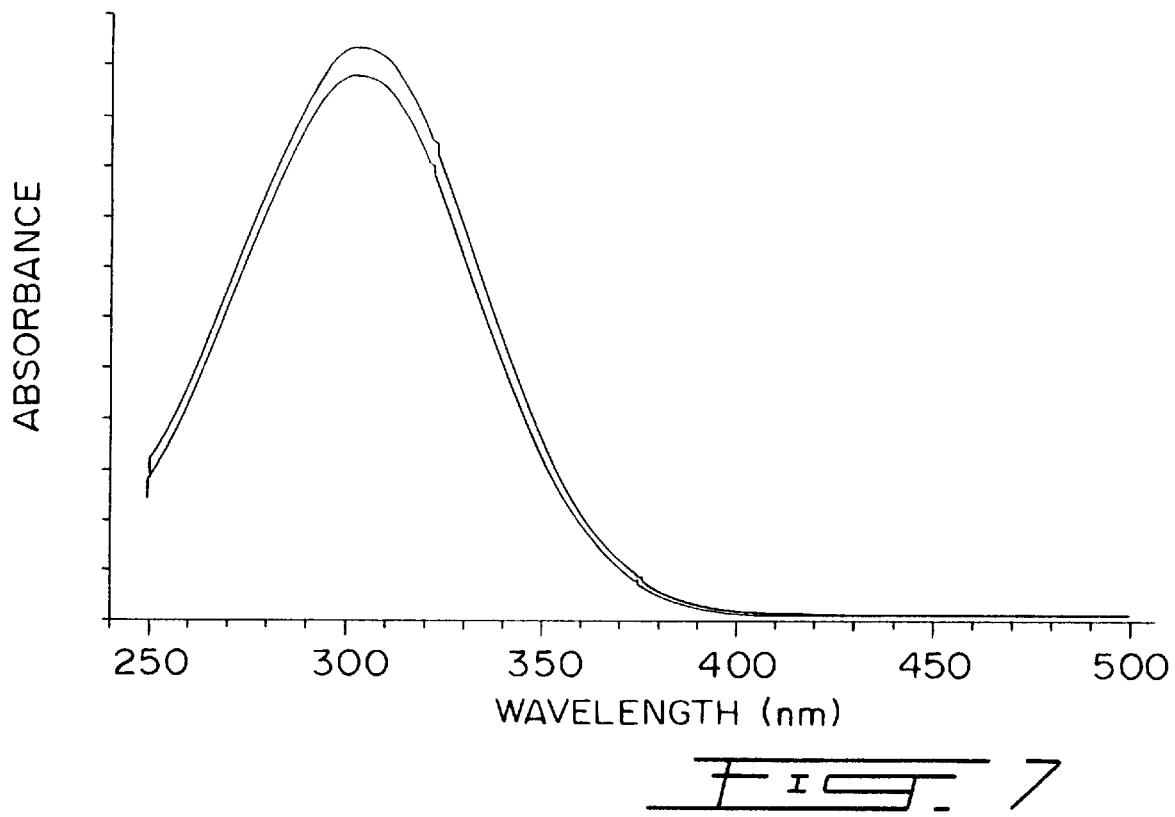
FIG. 7 is a UV spectrum showing initial evidence of the biological activity of a bioactive conjugate coating an implant prepared according to the present invention.
Figure 8:
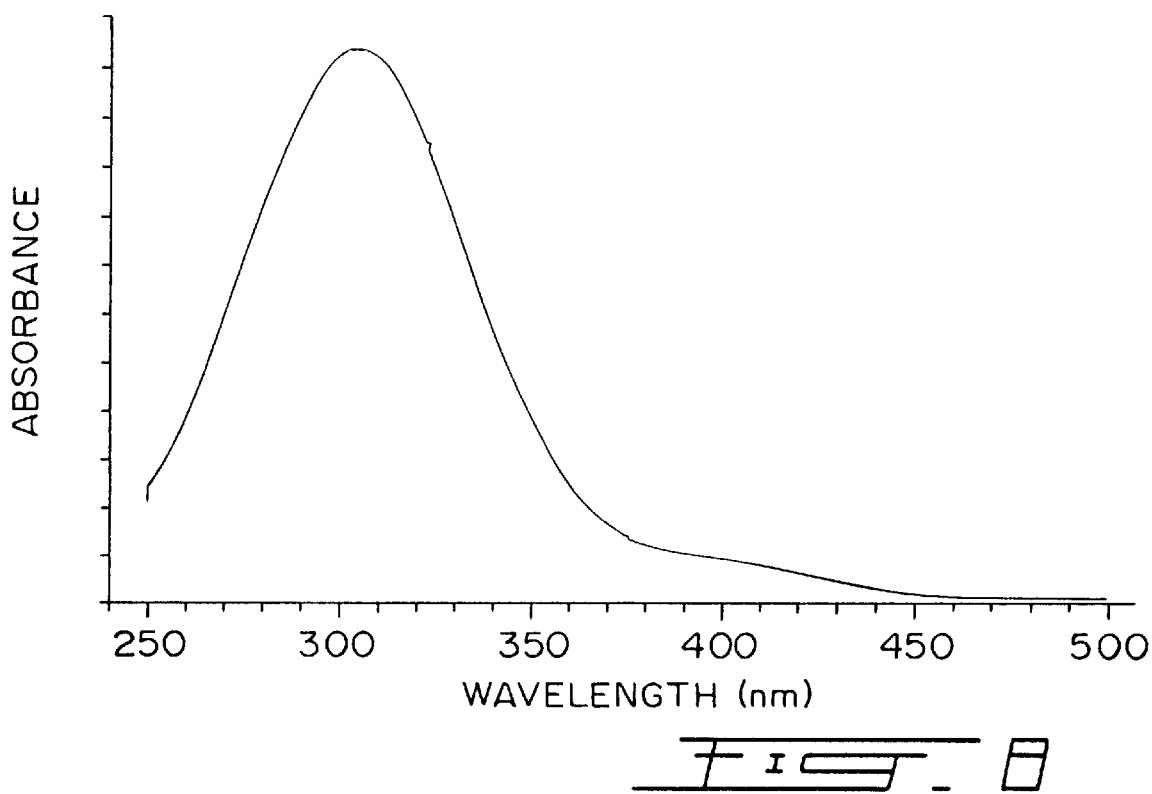
FIG. 8 is a UV spectrum showing evidence of the biological activity of the bioactive conjugate coating the implant after 14 hours of incubation.

FIG. 8 shows the appearance of a peak at 405 nm which provides clear evidence the alkaline phosphatase covalently-attached to the implant surface has retained its biological activity after 14 hours of incubation. Although, the peak at 405 nm is essentially absent from FIG. 7 which is taken near the beginning of the reaction, weak absorbance at 405 nm indicates initial stages of formation of p-nitrophenol by enzyme-catalysed hydrolysis.

EXAMPLE IV

Covalent Attachment of Alkaline Phosphatase to $TiO_2$

A sample of powdered $TiO_2$ equivalent in weight to that of a standard titanium implant was stirred for 2 h under $N_2$ with a 10% solution of 3-aminopropyltriethoxysilane in refluxing toluene. After centrifugation, rinsing with toluene, and drying, the modified $TiO_2$ was stirred for 60 min. at 25° C. under $N_2$ with a 2.5% solution of glutaraldehyde in 0.1M phosphate buffer.

After centrifugation and rinsing with 0.1M buffer, the modified $TiO_2$ was stirred for 12 h. at 25° C. with a solution of 3 mg alkaline phosphatase (from bovine intestinal mucosa, 5 units/mg) in 3 mL phosphate buffer. The modified $TiO_2$ was then rinsed thoroughly with buffer, and its enzymatic activity was measured by the method of Lowry et al. (*J. Biol. Chem.*, 164:321, 1946).

Figure 13:
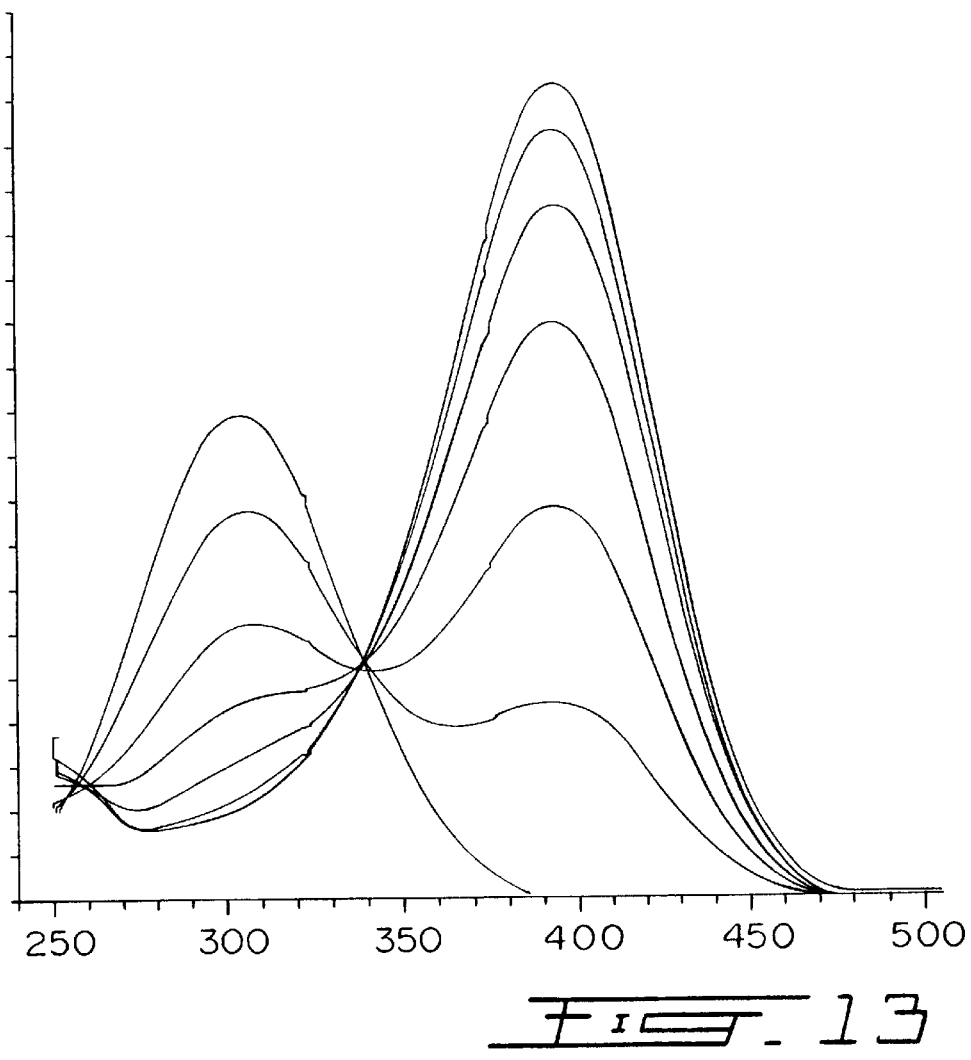
FIG. 13 represents a series of seven UV spectra of the surface of a titanium implant with alkaline phosphatase attached thereto.

FIG. 13 shows a series of seven UV spectra taken at 15 min. intervals from t=0 to t=90 min. during the course of an assay of a sample of modified $TiO_2$ using the method of Lowry. The peak near 305 nm, which corresponds to unhydrolyzed p-nitrophenyl phosphate, decreases continuously and is essentially absent at t=90 min. There is a corresponding increase in absorption near 395 nm, which corresponds to the formation of p-nitrophenolate. These spectra provide clear evidence for covalent attachment of alkaline phosphatase to $TiO_2$ in an enzymatically active form.

Figures 14A, 14B:
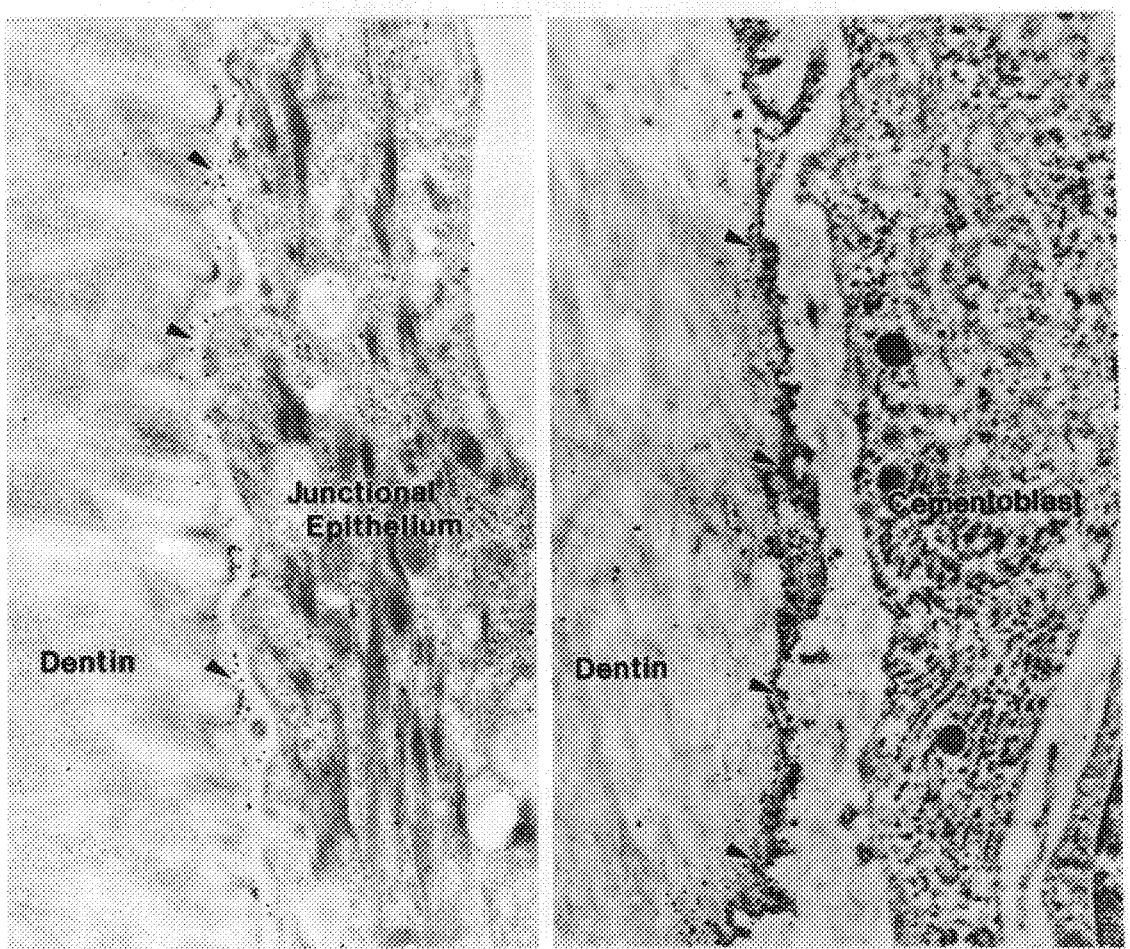
FIG. 14A illustrates a junctional epithelial cell in contact with surgically-exposed dentin showing the presence of enamel proteins (gold particles, arrowheads) interposed between the cell and the exposed dentin.
FIG. 14B is a micrograph illustrating a layer of osteopontin (gold particles, arrowheads) separating exposed dentin and a (pre)cementoblast.

For examining tissue repair and the production of new proteins at exposed mineralized tissue surfaces, we have used a model where the junctional epithelium is surgically detached (reflected) from the tooth surface and the palatal root of rat molars is exposed and the cementum and outermost dentin is removed from the root surface with a dental bur. Tissue healing in this circumstance occurs soon thereafter and comprises both a soft and hard tissue response in which two principal events occur. Firstly, junctional epithelium migrates down the tooth and over the damaged root surface and re-establishes an epithelial attachment. Coincident with the contact of these epithelial cells to the exposed dentin and/or cementum, enamel proteins (as indicated by immunoreactivity to antibodies raised against this epithelial secretory product) are secreted and accumulate as an organic layer at the root surface (FIG. 14A) adjacent to junctional epithelial cells. This class of protein is generally not believed to be expressed after completion of the enamel layer in unerupted teeth yet has here been shown to be part of the normal epithelial attachment (see FIG. 10B) and to be produced during reparation of this epithelial structure. Secondly, with regard to hard tissue formation and healing at these damaged sites in regions more apical to the epithelial cell migration, (pre)cementoblast are found against the tooth surface and are associated with the appearance of a layer of osteopontin (FIG. 14B) at the exposed root surface. This organic coating of osteopontin appears to be the initial event of reparative cementogenesis in which typical cementum then begins to fill in the defect at the root surface.

Figure 15:
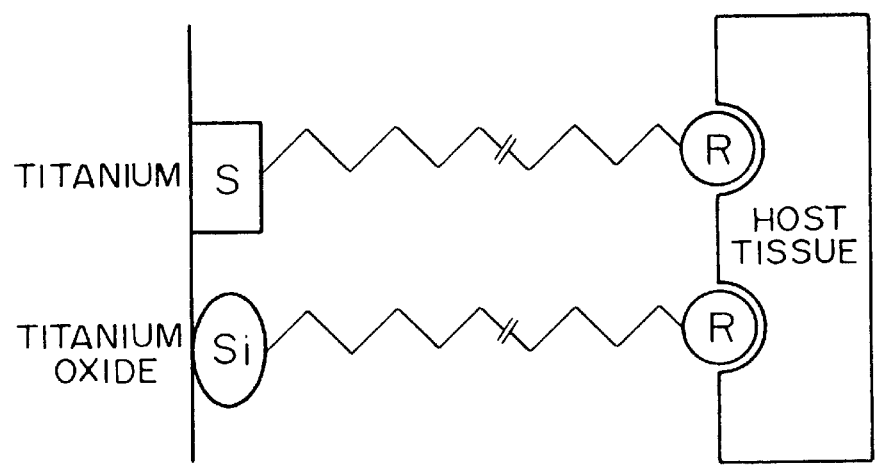
FIG. 15 is a scheme of a titanium surface implant coated in accordance with the present invention.

FIG. 15 is a scheme of a titanium surface implant coated in accordance with the present invention.

EXAMPLE V

Microfabrication

The synthesis of arrays of molecules on the planar metal surface of the present invention essentially relies on three fundamental processes: (1) covalent immobilization of molecules at a metal surface in accordance with the present invention; (2) in situ synthesis of molecules on the surface (self-assembly); and (3) physical entrapment of molecules in defined areas. Each of these processes can be scaled to micro- or nanometer dimensions.

The technology currently used for the fabrication of "molecular integrated circuits" can readily be adapted for molecular patterning at the micrometer scale. If specific electrochemical interaction or electrical signal measurement is required within a molecular array, then microelectrodes can be used as the molecular attachment sites. Alternatively, the lithographic techniques developed for integrated-circuit fabrication in the electronics industry can be adapted to pattern molecules and create "molecular integrated circuits".

The term "microelectrode", when used herein, is intended to mean any device which is derived from semiconductor technology but which is able to function in a physiological environment for electrical measurements at the cellular level in vitro or in vivo. Such microelectrodes, which may be used in accordance with the present invention, include 1) a titanium microelectrode cleaned and coated as described above; or 2) a microelectrode of the prior art coated with a thin layer of titanium which is then cleaned and coated as described above. Thus, in accordance with the present invention, the microelectrodes are not coated using polymers as opposed to the prior art techniques. Accordingly, the microelectrodes of the present invention, because they do not include polymers, present the advantage of direct attachment and precise orientation of molecules.

A cleaned metal implant surface as prepared according to the general procedure described in Example I can be used as an electrode for the preparation of such micro- or nanofabricated molecular integrated circuits or molecular arrays.

Photolithography enables the creation of devices or arrays to dimensions of ~2 $\mu$m in most clean-room facilities by the patterning and development of standard photoresists on planar surfaces. Dimensions smaller than this (to ~0.3 μm) can be achieved with more sophisticated optical lithography techniques currently used for the commercial synthesis of microelectronic chips (reviewed by P. Connolly, *TIBTECH*, 12:123–127, April 1994).

These devices are able to function in a physiological environment. For individual measurements at the cellular level, a suitable microelectrode should have dimensions of the order of a few micrometers, and most designs conform to this scale.

Another use of microelectrode-polymer arrays is the localized immobilization of molecules which is available for repetitive or successive interactions with cellular receptors or other molecules and which may trigger biochemical reactions as long as it remains immobilized. This may be used as a system in replacement of a controlled release system of drugs in situ, since the immobilized molecule of the present invention is available for more than one interaction and is an equivalent to the controlled release system.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. A titanium metal implant substantially free of impurities and having an outer surface coated with covalent attachment in a monolayer with a bioactive conjugate, which has the following structural formula I:

—R—X—P          I wherein,

R is S covalently attached to the titanium implant surface;

X is a linker covalently attached to R and selected from a bond, linear or branched chains of 1 to 30 covalently attached atoms of at least C, N, O, Si or S, rings of at least one of C, N, O, Si or S, and a combination thereof; and P is a bioactive molecule moiety stably attached to X via a covalent bond; said bioactive molecule moiety promoting tissue growth, stabilization or integration;

and wherein said bioactive moiety retains its biological activity.

2. An implant according to claim 1, wherein X is a bond, a linear alkyl $C_1$–$C_{30}$ chain, a linear chain consisting of from 1 to 20 C atoms interspersed with from 1 to 10 atoms of N, O or S, a ring composed of C and/or N, or a ring composed of C and/or N connected to a linear chain of C, N, O or S atoms, and X is terminated by a functional group which permits covalent linking to P.

3. An implant according to claim 2, wherein X is terminated by a functional group selected from COOH, $NH_2$, OH and SH.

4. An implant according to claim 1, wherein said bioactive conjugate forms a self-assembling monolayer on said implant surface.

5. An implant according to claim 1, wherein the covalently attached bioactive molecule moiety is selected from the group consisting of $\alpha_2$HS-glycoprotein and fibronectin.

6. An implant according to claim 11, wherein the covalently attached bioactive molecule moiety is selected from the group consisting of osteopontin, bone sialoprotein, bone acidic glycoprotein-75, osteocalcin, osteonectin, bone morphogenetic proteins, transforming growth factors, laminin, type IV collagen, type VIII collagen, enamel proteins, cell adhesion peptides, prostaglandins, serum proteins, glucocorticosteroids, phosphoserine, pyrophosphates, phosphothreonine, phosvitin, phosphophoryn, phosphonates, phosphatases and bone and epithelial proteoglycans.

7. An implant according to claim 6, wherein the covalently attached bioactive molecule moiety is selected from the group consisting of osteopontin and bone morphogenetic proteins.

8. An implant according to claim 6, wherein the covalently attached bioactive molecule moiety is selected from the group consisting of amelogenins and non-amelogenins.

9. An implant according to claim 6, wherein the covalently attached bioactive molecule moiety is a biphosphonate.

10. An implant according to claim 6, wherein the covalently attached bioactive molecule moiety is a peptide sequence selected from the group consisting of arginine-glycine-aspartic acid and polyaspartate.

11. A titanium metal implant substantially free of impurities and having an outer surface coated with covalent attachment in a monolayer with a bioactive conjugate, which has the following structural formula I:

—R—X—P          I wherein,

R is O covalently attached to the titanium implant surface;

X is a linker containing Si covalently attached to R and selected from a linear or branched chains of 1 to 30 covalently attached atoms of at least C, N, O, Si or S, rings of at least one of C, N, O, Si or S, and a combination thereof; and P is a bioactive molecule moiety stably attached to X via a covalent bond; said bioactive molecule moiety promoting tissue growth, stabilization or integration;

and wherein said bioactive moiety retains its biological activity.

12. An implant according to claim 11, wherein X is a linear alkylsilyl $SiC_1$–$SiC_{30}$ chain terminated by a functional group which permits covalent linking to P.

13. An implant according to claim 12, wherein X is terminated by a functional group selected from COOH, $NH_2$, OH and SH.

14. An implant according to claim 11, wherein the covalently attached bioactive molecule moiety is selected from the group consisting of $\alpha_2$HS-glycoprotein and fibronectin.

15. An implant according to claim 11, wherein the covalently attached bioactive molecule moiety is selected from the group consisting of osteopontin, bone sialoprotein, bone acidic glycoprotein-75, osteocalcin, osteonectin, bone morphogenetic proteins, transforming growth factors, laminin, type IV collagen, type VIII collagen, enamel proteins, cell adhesion peptides, prostaglandins, serum proteins, glucocorticosteroids, phosphoserine, pyrophosphates, phosphothreonine, phosvitin, phosphophoryn, phosphonates, phosphatases and bone and epithelial proteoglycans.

16. An implant according to claim 15, wherein the covalently attached bioactive moiety is selected from the group consisting of osteopontin and bone morphogenetic proteins.

17. An implant according to claim 15, wherein the covalently attached bioactive moiety is selected from the group consisting of amelogenins and non-amelogenins.

18. An implant according to claim 15, wherein the covalently attached bioactive moiety is a biphosphonate.

19. An implant according to claim 15, wherein the covalently attached bioactive moiety is a cell adhesion peptide.

20. An implant according to claim 15, wherein the covalently attached bioactive moiety is a peptide sequence selected from the group consisting of arginine-glycine-aspartic acid and polyaspartate.

* * * * *